United States Patent [19]
Bowen et al.

[11] Patent Number: 5,155,372
[45] Date of Patent: Oct. 13, 1992

[54] OPTICAL INSPECTION SYSTEM UTILIZING WEDGE SHAPED SPATIAL FILTER

[75] Inventors: Arlen J. Bowen; David L. Erickson, both of Rochester; Daniel W. Jewell, Pine Island; Venkat R. Koka, Rochester, all of Minn.

[73] Assignee: International Business Machines Corporation, Armonk, N.Y.

[21] Appl. No.: 797,877

[22] Filed: Nov. 26, 1991

[51] Int. Cl.$^5$ .............................................. G01V 9/04
[52] U.S. Cl. ................................ 250/571; 250/237 R; 359/562
[58] Field of Search .................. 250/571, 237 R, 572, 250/574, 575; 359/560, 561, 562, 564

[56] References Cited

U.S. PATENT DOCUMENTS

| | | | |
|---|---|---|---|
| Re. 27,491 | 9/1972 | Macovski | 359/562 |
| 3,729,252 | 4/1973 | Nelson | 359/562 |
| 3,748,047 | 7/1973 | Millgard et al. | |
| 3,972,616 | 8/1976 | Minami et al. | |
| 4,598,997 | 7/1986 | Steigmeier et al. | |
| 4,794,265 | 12/1988 | Quackenbos et al. | |
| 4,861,164 | 8/1989 | West | |
| 4,927,267 | 5/1990 | Herve | |

Primary Examiner—David C. Nelms
Assistant Examiner—Que T. Le
Attorney, Agent, or Firm—Duke W. Yee

[57] ABSTRACT

The present invention includes a system for monitoring surface structures on a planar surface utilizing a radiation source emitting a beam. The planar surface has various surface structure types, including a plurality of grooves therein which intersect at various angles which are equal to or less than a predetermined maximum angle. The system includes an apparatus for directing the beam to the planar surface along an optical axis perpendicular to the planar surface resulting in radiation being scattered from the planar surface and a reference beam being specularly reflected from the planar surface. The system also includes detector responsive to radiation scattered from the planar surface. This detector produces a first signal representative thereof. Also provided is a spatial filter for filtering radiation scattered from the planar surface to allow only radiation from at least selected one of the plurality of surface structure types to reach the detector responsive to radiation scattered from the planar surface. The system may also include a detector responsive to the reference beam, producing a second signal in response to the reference beam and a circuit for producing a final signal from the first signal and the second signal.

16 Claims, 6 Drawing Sheets

OPTICAL INSPECTION SYSTEM UTILIZING WEDGE SHAPED SPATIAL FILTER

BACKGROUND OF THE INVENTION

1. Field of the Invention

The present invention relates generally to an improved system for inspecting textured surfaces and detecting defects, and particulate contaminants on a surface and in particular to an improved method and system for inspecting textured surfaces, with improved resolution. Still more particularly, the present invention provides an improved system for inspecting textured surfaces and detecting defects, and contaminants on such a surface through the use of a shaped spatial filter and a reference optical beam.

2. Description of the Related Art

Disks used for recording data may contain various surface structures such as defects, particulate contaminants, and surface texture. Presently, the high-recording densities on thin-film disks and the head/disk tribology require that the disks be free of defects and particulate contaminants. Most defects and contaminants, which were previously acceptable on particulate-oxide media disks, are unacceptable on thin-film disks. To detect such fine defects and contaminants, high-resolution instruments are required.

In addition, texturing of disks is required to control stiction properties of the disk. Texture is intentionally added to a disk to provide low friction or "stiction" when a magnetic head is sliding or resting on the disk. Presently, disk drive motors are very small, resulting in an inability to spin the disks up to a proper speed if too much friction or stiction is present. Therefore, it is critical to maintain a proper level of friction or stiction. Older disks drives possessed enough power such that friction or stiction was not as much of a concern.

Prior to the present invention, the level of texture or roughness was monitored with a mechanical stylus instrument that contacted the surface of the disk. This type of instrument, involving a contact method, is slow and time consuming. As a result, it is not economically possible to test every disk manufactured. As a result, disks were sampled and assumptions were made that the remainder of the disks in the sample group were of the same texture. This assumption, however, is not accurate since small changes in a manufacturing process may change the texture. Some systems have been developed to measure texture by collecting and measuring light scattered from a disk due to the texturing. Integrating spheres have been utilized, however, such spheres collect light from all structures on the disk which scatter light. This results in errors since the scattered light includes scattering, as a result of the textured surface, previous polishing, carbon impurities, and other microstructures or particles.

Therefore, it would be desirable to have a method and system capable of collecting and measuring light scattered off a disk surface as a result of the texture of the surface or defects and particles on the surface.

SUMMARY OF THE INVENTION

It is therefore one object of the present invention to provide an improved system for inspecting textured surfaces and detecting defects, and particulate contaminants on a surface.

It is another object of the present invention to provide an improved apparatus for inspecting textured surfaces and detecting defects, and particulate contaminants on a surface with improved resolution.

It is yet another object of the present invention to provide an improved system for inspecting textured surfaces and detecting defects, and particulate contaminants on a surface through the use of a shaped spatial filter.

It is a further object of the present invention to provide an improved system for inspecting textured surfaces and detecting, defects, and particulate contaminants on a surface through the use of a reference beam.

The foregoing objects are achieved as is now described. The present invention includes a shaped spatial filter for selectively filtering scattered radiation created as a result of a source radiation beam striking a planar surface having a plurality of grooves therein which intersect at various angles which are equal to or less than a predetermined maximum angle. The shaped spatial filter preferably includes a first nontransmissive area having a predetermined width for blocking direct reflection of the source radiation beam from the planar surface. The filter also includes at least one radially disposed substantially wedge-shaped transmissive area extending outward from the first nontransmissive area. This radially disposed transmissive area has a width equal to the predetermined width at a point proximate to the first nontransmissive area and increases in width at a selected angle from a bisector of the radially disposed substantially wedge-shaped transmissive area. The selected angle is substantially equal to the predetermined maximum angle of intersection of the surface grooves.

The present invention also includes a system for monitoring surface structures on a planar surface utilizing a radiation source emitting a beam. The planar surface has various surface structure types, including a plurality of grooves therein which intersect at various angles which are equal to or less than a predetermined maximum angle. The system includes an apparatus for directing the beam to the planar surface along an optical axis perpendicular to the planar surface resulting in radiation being scattered from the planar surface and a reference beam being specularly reflected from the planar surface. Also included is a detector responsive to radiation scattered from the planar surface. This detector produces a first signal representative thereof. Also provided is a shaped spatial filter for filtering radiation scattered from the planar surface to allow only radiation from at least selected one of the surface structure types to reach the detector responsive to radiation scattered from the planar surface.

The system may also include a detector that is responsive to the reference beam, which produces a second signal in response to the reference beam and circuit for producing a final signal from the first signal and the second signal.

The above as well as additional objects, features, and advantages of the present invention will become apparent in the following detailed description.

BRIEF DESCRIPTION OF THE DRAWING

The novel features believed of the invention are set forth in the appended claims. The invention itself, however, as well as a preferred mode of use, further objects and advantages thereof, will be best understood by reference to the following detailed description and the accompanying drawings, in which:

DETAILED DESCRIPTION OF THE INVENTION

Figure 1:
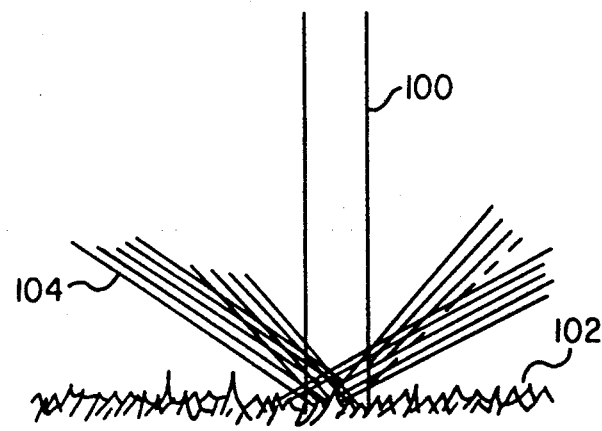
FIG. 1 depicts a side view of a pattern of scattered light from a textured disk.

With reference now to the figures, and in particular with reference to FIG. 1, there is depicted a side view of a pattern of scattered light from a textured disk. A laser beam 100 with a predetermined spot size is focused on a textured disk surface 102 with laser beam 100 being perpendicular to surface 102. If surface 102 was perfectly smooth and defect-free, laser beam 100 would be reflected specularly. Localized surface irregularities and particulate contaminants on surface 102, however, will scatter a fraction of light from laser beam 100 as scattered light 104.

Figure 2:
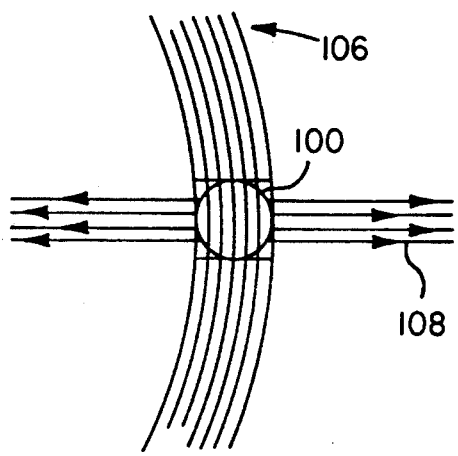
FIG. 2 is a top view illustrating a pattern of scattered light from a circumferential texture on a disk.

FIG. 2 is a top view illustrating a pattern of scattered light from a circumferential texture on a disk. Circumferential texture 106 contains texture ridges or grooves that are almost concentric to each other. Assuming that the ridges or grooves are defect and particle free, circumferential texture 106 will scatter light from laser beam 100 in a radial direction as radially scattered light 108.

Figure 3:
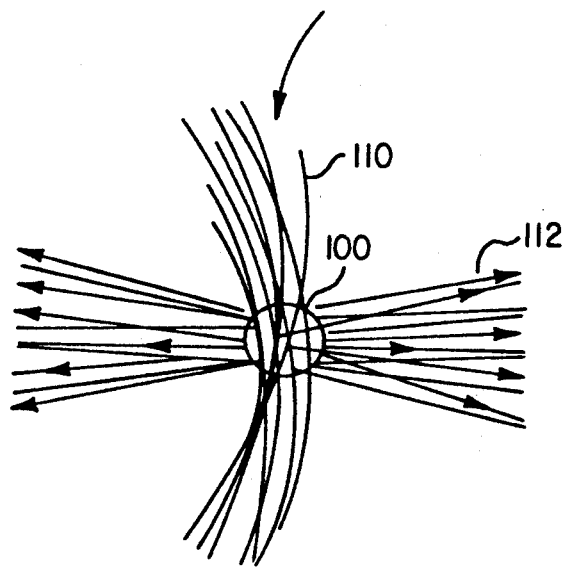
FIG. 3 depicts a top view illustrating a pattern of scattered light from a cross hatched texture on a disk.

FIG. 3 depicts a top view illustrating a pattern of scattered light from a cross hatched texture on a disk. Cross hatch texture 110 is a texture that deviates from circumferential texture 106 at different positive and negative angles. The ridges or grooves intersect at various angles. A cross hatch texture of 10° would contain ridges or grooves intersecting at various angles less than or equal to 10°. Cross hatch texture 110 can be produced by spinning a smooth disk and placing an abrasive tape on the disk and moving it radially back and forth at a predetermined rate. Changing the speed of the disk and the movement of the tape will change the cross hatch texture. Focusing laser beam 100 on the disk surface containing cross hatch texture 110 results in scattered light 112. Scattered light 112 is in the shape of a bow tie or a pair of winglets. The exact shape depends on the maximum angle of cross hatching and on the type of roughness.

Figure 4:
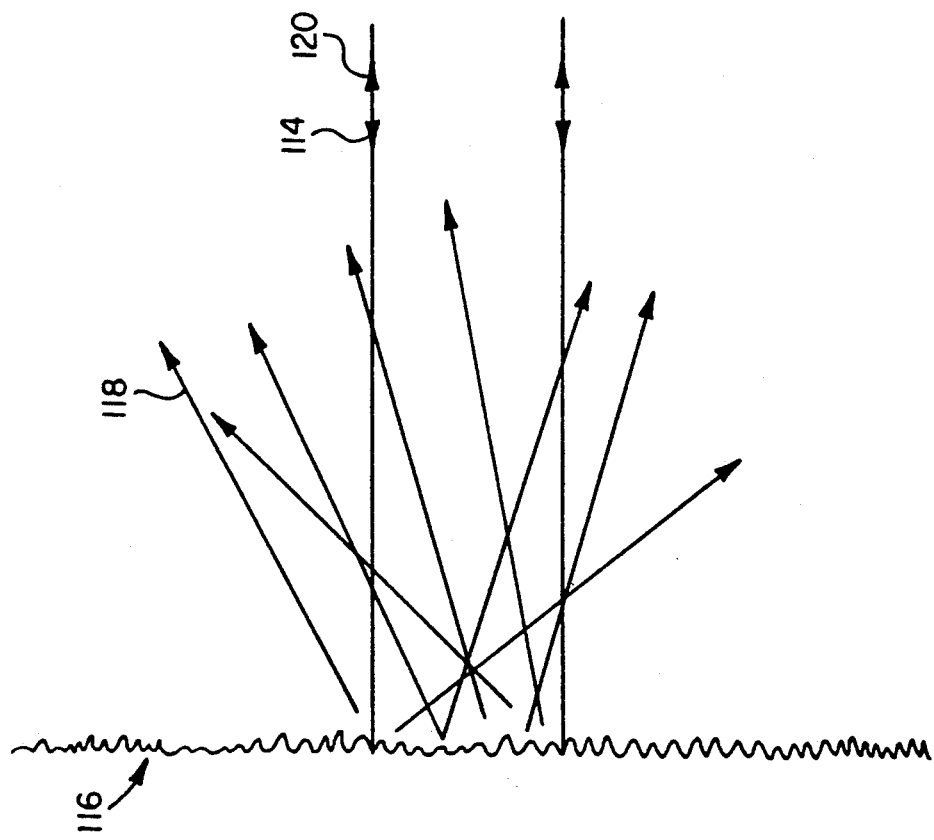
FIG. 4 is a near field, side view of a textured surface with a 10° cross hatch texture.

FIG. 4 is a near-field, side view of a textured surface with a 10° cross hatch texture. Laser beam 114 strikes textured surface 116 which has a 10° cross hatch. A portion of laser beam 114 is scattered by textured surface 116 as scattered light 118. The rest of laser beam 114 is reflected as reflected laser beam 120.

Figure 5:
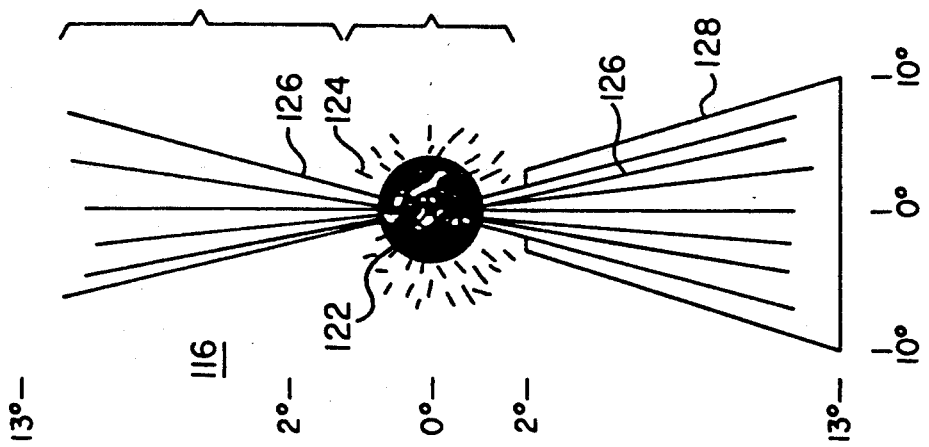
FIG. 5 depicts a far-field, optical access view illustrating a pattern of scattered light from a 10° cross hatch textured surface.

FIG. 5 depicts a far-field, optical axis view illustrating a pattern of scattered light from a 10° cross hatch textured surface on a disk. When laser beam 122 strikes textured surface 116 some of the light from the laser beam is scattered by textured surface 116 and the remainder of the light is reflected. From about zero to one degree off the axis of laser beam 122, the scattered light includes both nontexture scattered light 124 and texture scattered light 126. Beyond one degree off the optical axis of laser beam 122, only texture scattered light 126 is found; texture scattered light 126 spreads out, radially in relation to the disk, above and below the optical axis of laser beam 122 in the shape of a bow tie or a pair of winglets. Textured scattered light 126 typically extend 13° in each direction from the central beam. In designing a spatial filter for obtaining light scattered from surface textures, the majority of the useful information extends 1° to 13° off the optical axis. Textured scattered light 126 spreads out to the left and the right of the optical axis of laser beam 122 by 10°.

The spreading out of texture scattered light 26 is a function of the maximum degree of cross hatching on textured surface 116. For example, if textured surface 116 had a maximum cross hatching of 15°, texture scattered light 126 would spread out to the left and right of optical axis of laser beam 122 by 15°.

It is desirable in one embodiment of the present invention to filter out nontexture scattered light 124 and light reflected from laser beam 122. In such an embodiment, spatial filter 128 is utilized to filter texture scattered light 126. Spatial filter 128 is shaped to pass or transmit only texture scattered light 126. In a preferred embodiment of the present invention, the spatial filter would pass light from 2° to 13° below and above the optical axis of laser beam 122. Although, texture scattered light is found between one and two degrees off the optical axis of laser beam 122 and generally no nontexture scattered light 124 is found in this region, it is preferred to make this region a "deadband" to allow for occurrences of unusual nontexture scattered light to occur.

Figure 6:
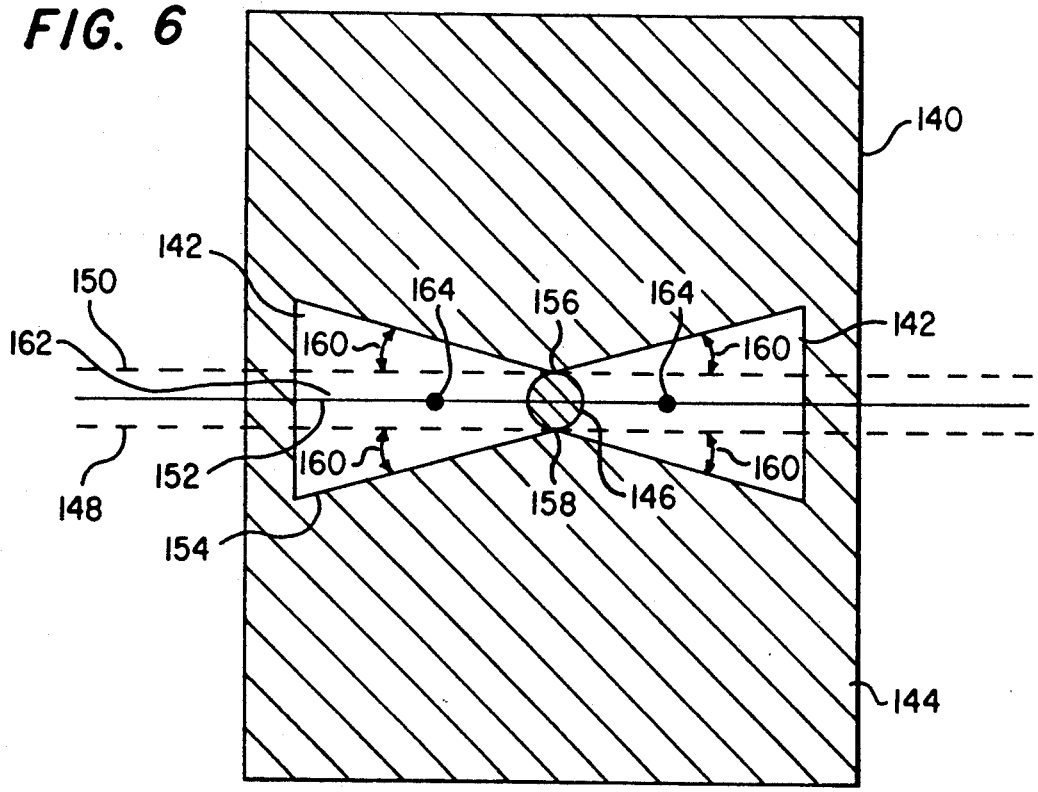
FIG. 6 is a spatial filter for passing light scattered by a cross hatch textured surface in accordance with a preferred embodiment of the present invention.

FIG. 6 is a spatial filter for passing light scattered by a cross hatch textured surface in accordance with a preferred embodiment of the present invention. The amount of light scattered by a contaminant/defect free surface is a function of the root mean square roughness of the surface. Consequently, measuring scattered light from the texture alone will yield a measure of roughness. Spatial filter 140 contains a transmissive section 142 and a nontransmissive section 144. Transmissive section 142 is shaped or configured to allow texture scattered light to be transmitted to a detector. The remainder of spatial filter 140 contains nontransmissive section 144 which prevents or blocks the transmission of texture scattered light to a detector.

The shape of transmissive section 142 is generally that of a bow tie or two winglets. Nontransmissive section 144 has a circular portion 146 that is aligned coincidental with an axis along which a reflected laser beam travels. The reflected laser beam originates from the original laser beam striking a textured surface. The reflected laser beam has a circumference which is a function of the spot size of the original laser beam and the circumferential roughness of the disk. Further circular section 146 is also configured in size and shape to block transmission of the reflected laser beam.

Transmissive section 142 extends to the right and left of circular portion 146 to terminate in a right and left side, positioning lines, positioning line 148 and positioning line 150, are utilized to define upper edge 152 and lower edge 154 of transmissive section 142. Positioning line 148 extends horizontally from point 156 and positioning line extends horizontally from point 158. Point 156 and point 158 are diametrically opposed on circular portion 146. Upper edge 152 extends to the right and to the left of circular portion 146 at an angle theta 160 included between positioning line 150 and side 152. Lower edge 154 also extends to the right and to the left at an angle theta 160 included between positioning line 148 and lower edge 154. Angle theta 160 is determined by the maximum cross hatching angle of the textured surface.

Upper edge 152 and lower edge 154 may be defined also by reference to a bisector line 162 horizontally bisecting circular portion 146 wherein upper edge 152 and lower edge 154 each spread out at angle theta 160 from bisector line 162 at point 164.

Figure 7:
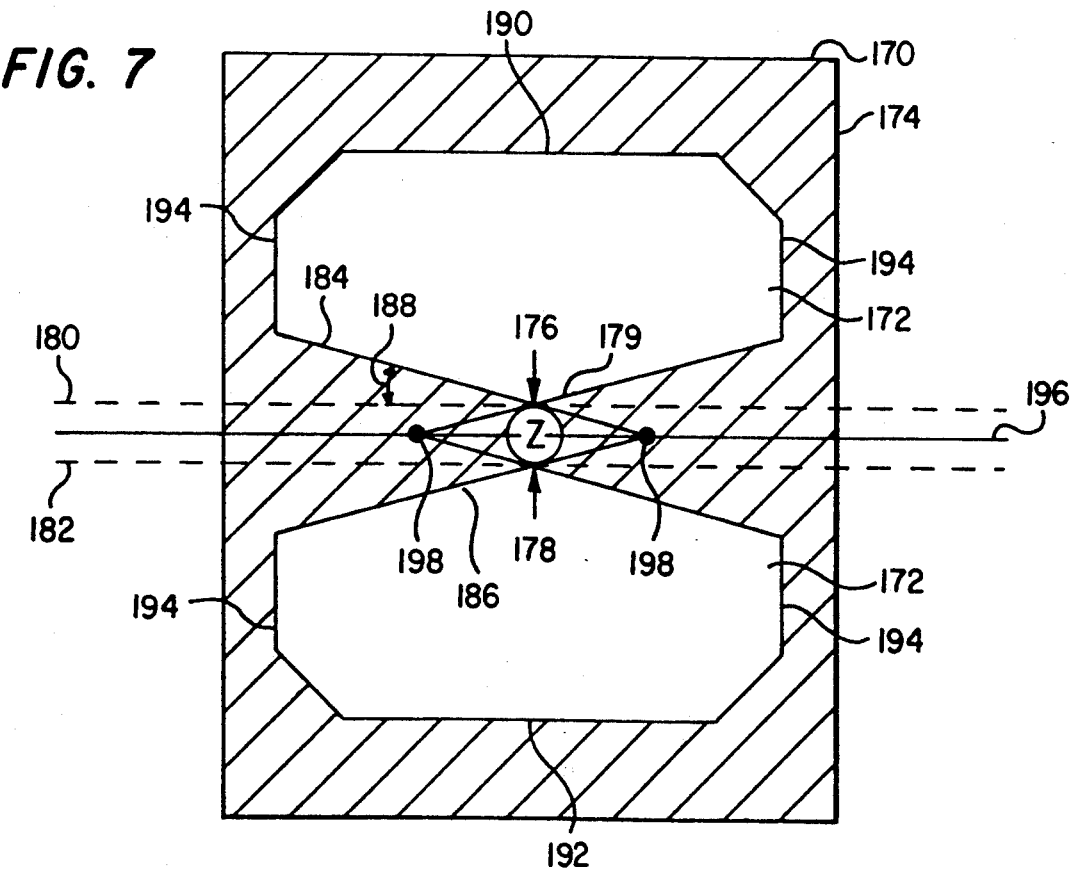
FIG. 7 depicts a spatial filter for passing light scattered by defects and particulate contaminants on a cross hatch textured surface in accordance with a preferred embodiment of the present invention.

FIG. 7 depicts a spatial filter for passing light scattered by defects and particulate contaminants on a cross hatch textured surface in accordance with a preferred embodiment of the present invention. Spatial filter 170 has a transmissive section 172 and a nontransmissive section 174. In this particular embodiment, the transmissive section 172 and nontransmissive 174 are reversed from transmissive section 142 and nontransmissive section 144 of spatial filter 140 in FIG. 6. The nontransmissive section has a center section defined by point 176 and point 178. Point 176 and point 178 are diametrically aligned On the radial edge of a circular section 179 Corresponding in size to the reflected beam. Positioning line 180 extends horizontally from point 176 and positioning line 182 extends horizontally from point 178. Nontransmissive section 174 has an upper edge 184 and a lower edge 186. Upper edge 184 extends from point 176 towards the right and left; lower edge 186 extends from point 178 to the right and the left. Upper edge 184 extends at an angle theta 188 from positioning line 180. Lower edge 186 also extends to the right and the left at an angle theta 188 from positioning line 182 starting at point 178. The transmissive section 172 has a top edge 190, a bottom edge 192, and a plurality of sides 194. Top edge 19?, bottom edge 192, and sides 194 are normally defined in shape by the shape of the detector. For example, if the detector was circular in shape, top edge 190 and sides adjacent to top edge 190 would actually form a semicircle as would bottom edge 192 and sides associated with bottom edge 192.

Upper edge 184 and lower edge 186 may also be defined by a bisector line 196 wherein upper edge 184 and lower edge 186 each spread out at an angle theta 188 from bisector line 196 at point 198.

Figure 8:
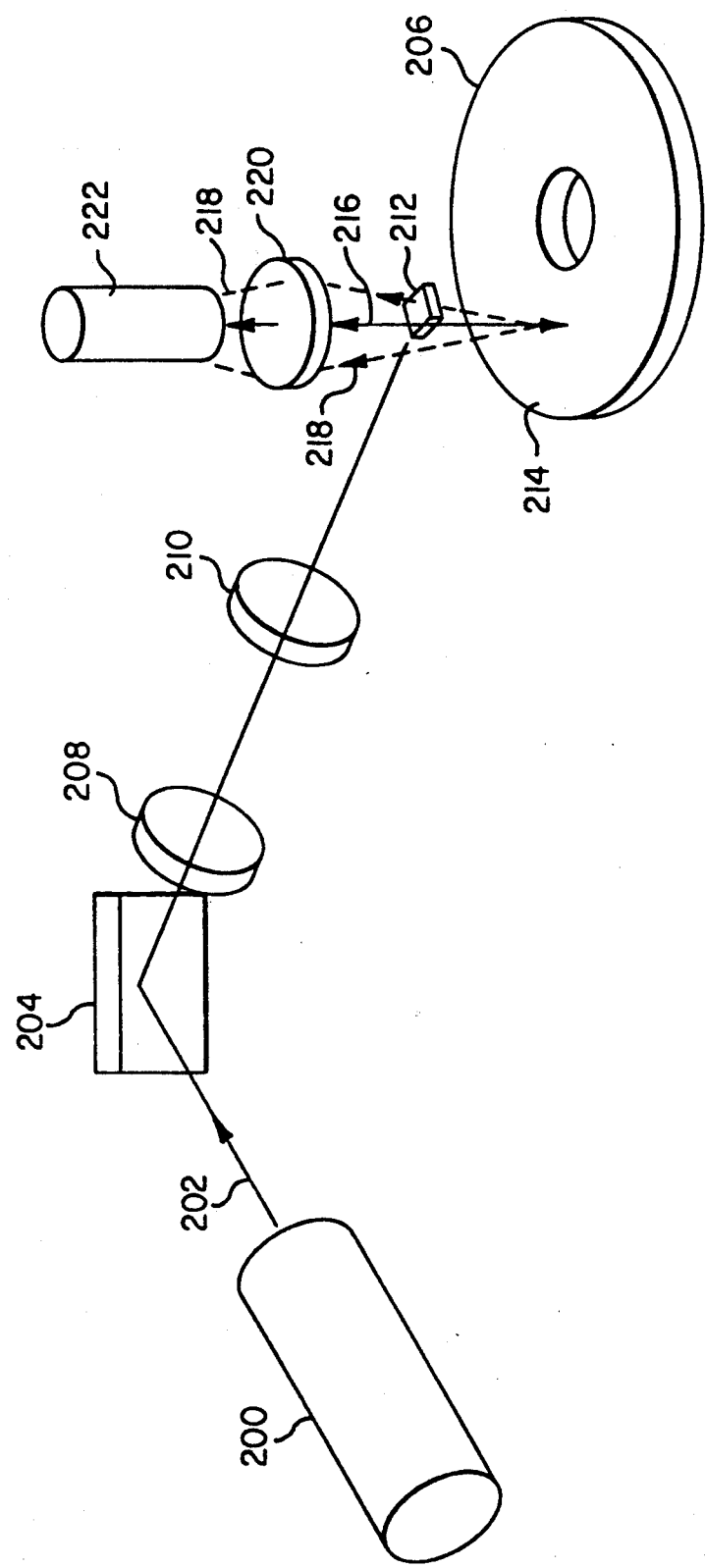
FIG. 8 is a perspective view of a system for detecting surface texture, defects, and particulate contaminants in accordance with a preferred embodiment of the present invention.

FIG. 8 is a perspective view of a system for detecting surface texture, defects, and particulate contaminants in accordance with a preferred embodiment of the present invention. In accordance with a preferred embodiment of the present invention a laser 200 emits a laser beam 202 that is directed by a mirror 204 towards a disk 206. Focusing lens 208 and 210 are utilized to maintain the width of laser beam 202. Mirror 212 directs laser beam 202 onto surface 214 of disk 206. At this point, laser beam 202 travels along an axis substantially perpendicular to surface 214. A portion of laser beam 202 is reflected as a reflected laser beam 216. Scattered light 218 is scattered from surface 214 by surface irregularities and particulate B contaminants. Reflected laser beam 216 and scattered light 218 pass through focusing lens 220 into detector 22. If it is desired to detect defects or particulate contaminants or other artifacts other than surface texture, a spatial filter such as the spatial filter depicted in FIG. 7 would be placed in front of detector 222.

The placement of a spatial filter would block light scattered by surface textures found on surface 214, but would allow light scattered by defects, particulate contaminants, or other artifacts other than surface texture on surface 214 to be transmitted to detector 222. Other sources of scattered light and reflected beam 216 would also be prevented from reaching detector 222 by nontransmissive areas of the spatial filter. If detecting surface texture on surface 214 of disk 206 is desired, the spatial filter described in FIG. 6 is utilized to allow transmission of light scattered by surface textures and blocking transmission of light scattered by defects, particulate contaminants, or other artifacts not caused by surface texture on surface 214.

Figure 9:
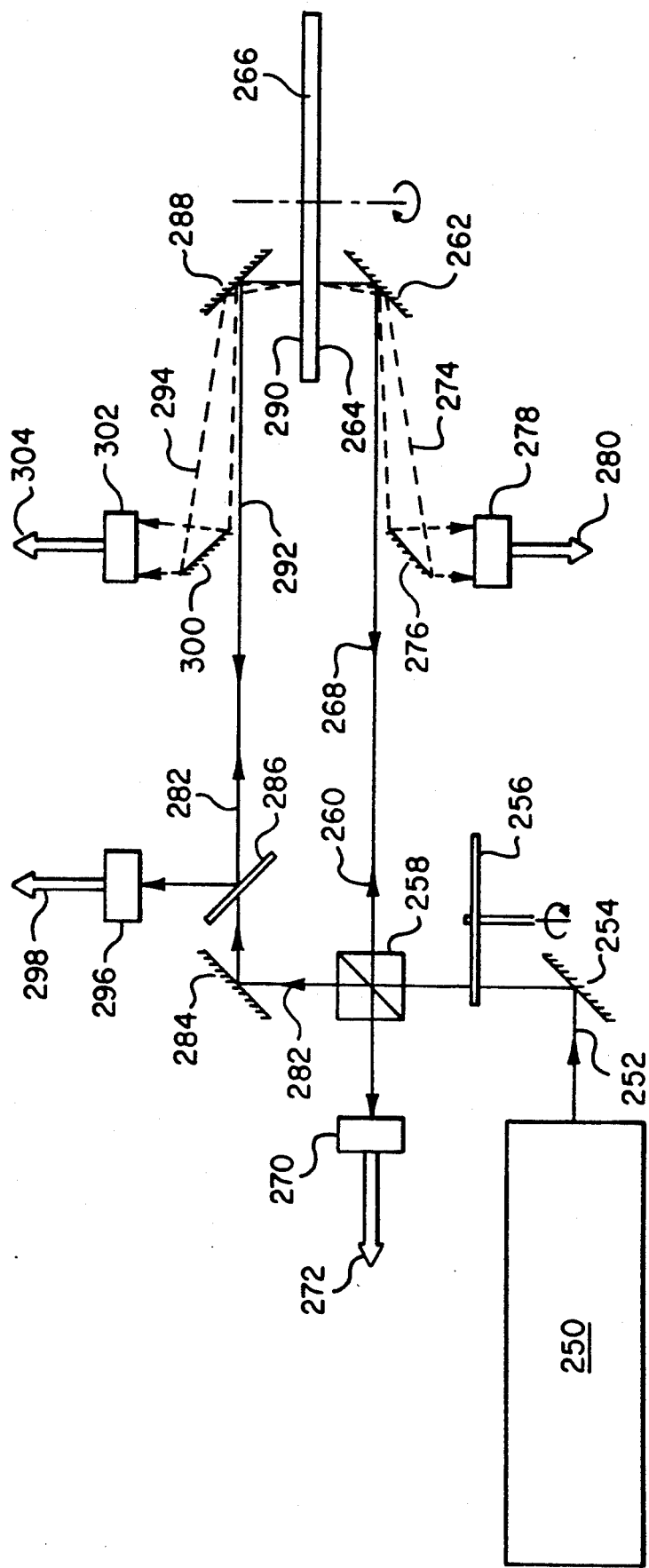
FIG. 9 depicts a side view of a system for detecting surface texture in accordance with a preferred embodiment of the present invention.

FIG. 9 depicts a side view of a system for detecting surface texture in accordance with a preferred embodiment of the present invention. A HeNe laser 250 emits a 1.0 mW laser beam 252 which is directed by mirror 254 through chopper 256, and laser beam 252 is split by beam splitter 258 into two 0.5 mW laser beams. Chopper 256 is utilized for synchronistic detection for signal 304 and signal 280. Chopper 256 permits leakage current from the photodiode to be taken out. Laser beam 260, having a power of 0.5 mW, is directed by mirror 262 perpendicular to side 264 of disk 266. Laser beam 260, reaching side 264 results in a reflected beam 268. Reflected beam 268 is about 0.495 mW in power.

Reflected beam 268 travels through beam splitter 258 t o reach photodiode 270. The power of laser beam 268 after passing through beam splitter 258 is about 0.248 mW. Photodiode 270 receives reflected beam 268 and causes a signal 272 to be produced. Part of laser beam 260 is scattered when laser beam 260 reaches side 264. Scattered light 274 is directed by mirror 262 to mirror 276, which in turn directs scattered light 274 to photodiode 278. The power of the scattered light reaching photodiode 278 is about 0.0025 mW. Photodiode 278 produces signal 280 in response to receiving scattered light 274.

Beam splitter 256 also splits laser beam 252 into to beam 282 which is a 0.5 mW laser beam. Beam 282 is directed by mirror 284 through beam splitter 286, resulting in the beam's power being reduced to 0.46 mW. Beam 282 travels to mirror 288 where beam 282 is directed onto surface 290 of disk 266. Beam 282 is directed substantially perpendicular to surface 290 by mirror 288 which results in a reflected beam 292 and scattered light 294. Reflected beam 292 is directed by mirror 288 along the same axis as beam 282 where it is directed by beam splitter 286 into photodiode 296.

In response to receiving reflected beam 292, photodiode 296, converts reflected beam 292 into a signal 298. Scattered light 294 is directed by mirror 288 to mirror 300 which in turn directs scattered light 294 into photodiode 302. In response to scattered light 294, photodiode 302 produces a signal 304.

Figure 10:
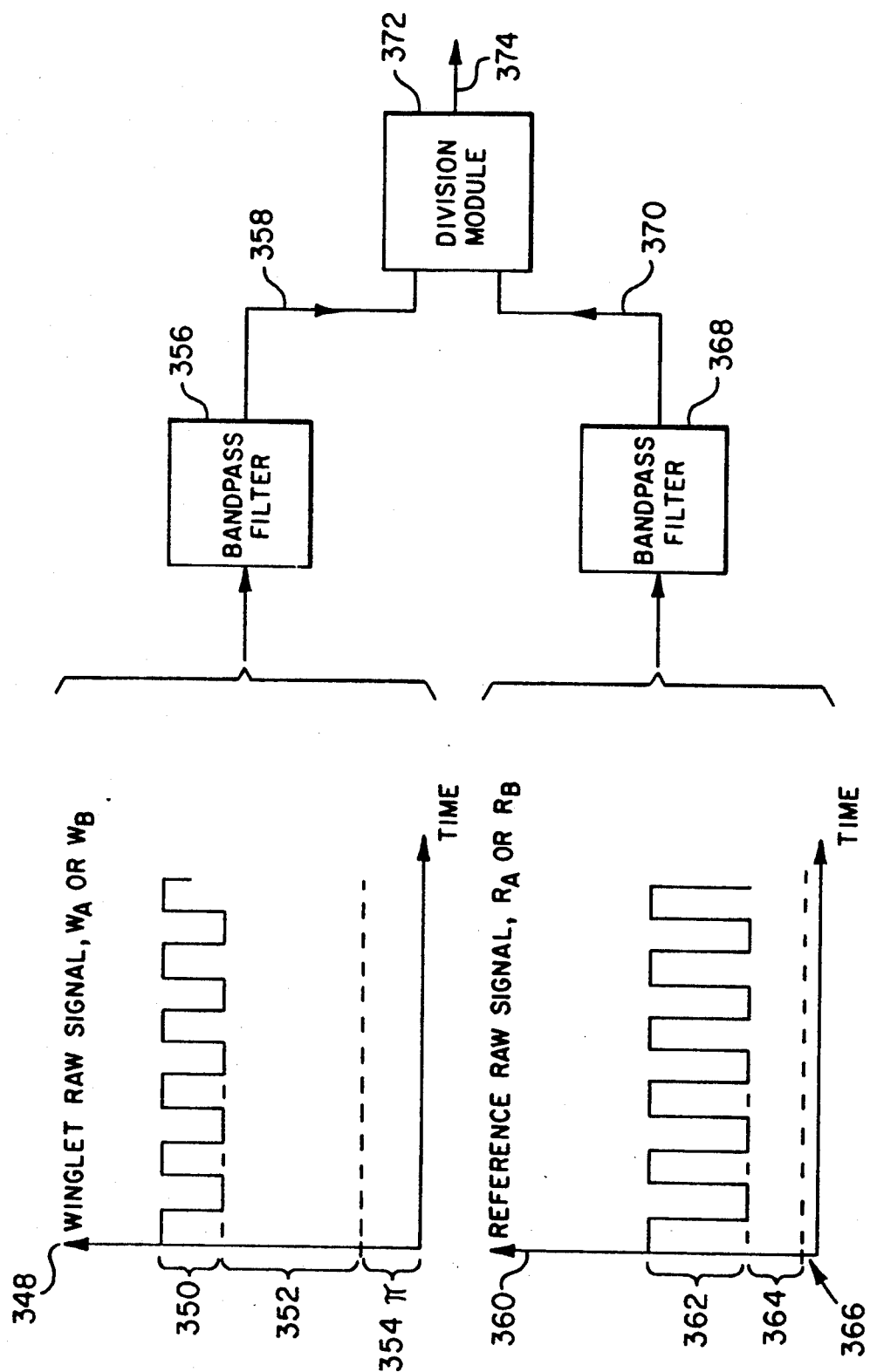
FIG. 10 is a schematic diagram of a system for processing signals from the system depicted in FIG. 9 in accordance with a preferred embodiment of the present invention.

FIG. 10 is a schematic diagram of a system for processing signals from the system depicted in FIG. 9 in accordance with a preferred embodiment of the present invention. Signal 280 and signal 304 are raw data signals from light collected at the photodiodes from light scattered by surface textures on the surface of the disk.

These raw signals include data from carbon times texture 350 extraneous light and leakage current 354. Leakage current 354 is the leakage current from the photodiode that receives scattered light. The carbon part of carbon times texture 350 includes various materials covering the disk such as magnetic material, the carbon overcoat, and the lubricant. The majority of the material covering the disk comprises carbon transparency. This carbon transparency is a transparent carbon overcoat and affects results during analysis. Since the carbon transparency reflects from about 50% to 97% of the light this carbon overcoat can vary the results by a factor of two. The magnetic metal usually reflects about 99% of the light and does not cause as much variation in readings. The same holds true for the lubricant as in the case of the magnetic metal.

Raw signal 348 is passed through bandpass filter 356. As a result, processed signal 358 only contains carbon times texture 350.

Raw reference signal 360 corresponds to signal 298 or signal 272. This signal contains data from carbon 362, extraneous light 364, and leakage current. 366. The carbon in raw reference signal 360 corresponds to the carbon in carbon times texture 350. Leakage current 366 is the leakage current from the photodiode that receives the reflected laser beam. Extraneous light 364 comes from light sources other than the laser beam.

Raw reference signal 360 is passed through a bandpass filter 368. After passing through bandpass filter 368, only carbon 362 remains in processed signal 370. Processed signal 358 and processed signal 370 are sent through a division circuit 372 which divides out the carbon information from processed signal 358. As a result, final signal 374 contains only texture information and is sent on for determining texture characteristics of the surface.

Signal 298 would be used as a raw reference with signal 304 as the similarly signal 272 would be the raw reference signal processed with signal 280 as the raw signal.

A bandpass filter is depicted in this particular embodiment, but other techniques will be known by those skilled in the art for removing extraneous light and leakage current from processed signal 358 and processed signal 370. For example, a sample and hold circuit may be used or synchronistic detection techniques may be utilized to remove extraneous light and leakage current. Another circuit that may be utilized in place of a bandpass filter is a negative following circuit or a dark following circuit. In essence the raw signal from the scattered light is divided by the reference signal in order to produce a net signal for analysis to determine the surface texture on the disk being sampled to determine whether it corresponds to the tolerances set during manufacturing.

Linear correlation has been found between the method and system of the present invention for measuring textured surfaces and a mechanical stylus system using a RMS roughness.

The spatial filter under a preferred embodiment of the present invention may be placed in front of a mirror reflecting light to a detector such as mirror 300 and mirror 276 in FIG. 9. Alternatively the spatial filter could be placed directly over the photodiode or detector such as photodiode 278 and photodiode 302 in FIG. 9.

Utilizing the method and system in accordance with the present invention results in a much quicker measurement time as compared to a mechanical stylus system. As a result, all the disks in a batch may be tested opposed to sampling a few disks out of a batch and assuming all the disks are exactly the same.

Reflected beam 266 and reflected beam 292 are utilized as reference beams to correlate signals obtained from scattered light to RMS roughness obtained from the stylus signal. The signal from the scattered light is divided into the reference beam in order to make the correlation. The reference beam must be collected after beam 260 or beam 282 hits disk 266. The reason for obtaining a signal from a reference beam after the laser beam hits the disk is to account for differences due to carbon overcoats, magnetic metals, and lubricants put on the disk. These materials covering the disk attenuate or scatter the light by the same ratio as it attenuates the reference beam.

Consequently the reference beam may be utilized to remove this attenuation as shown in FIG. 10. If a reference beam is obtained prior to striking disk 266, no attenuation would result making any normalization of the signals from scattered light less accurate than if the reference beam is acquired after laser beam 260 or laser beam 282 strikes disk 266.

Basically, the signal from the winglet or bowtie is divided by the reference beam to obtain an accurate percent reflection from the surface of the disk.

Consequently disks may be measured with lubricant or without lubricant, with carbon or without carbon and obtain accurate results without having to change a calibration signal. Measurement accuracies in the tenth of angstroms may be obtained utilizing a preferred embodiment of the present invention.

The disk may be spinning or stepped during measurement of the disk. Also, a particular cross hatch texture may be detected on disks by first obtaining data from a desired cross hatching on a disk. Then comparing the data to data obtained from disks which should have the same texture.

It is also contemplated that some other source of radiation other than a laser could be utilized in accordance with the present invention. Another source of radiation would require that the emitted beam be scattered by the surface being monitored or tested. The radiation source should be able to emit a focused beam of radiation or a coherent beam of radiation.

While the invention has been particularly shown and described with reference to a preferred embodiment, it will be understood by those skilled in the art that various changes in form and detail may be made therein without departing from the spirit and scope of the invention.

What is claimed is:

1. A spatial filter for selectively filtering scattered radiation created as a result of a source radiation beam striking a planar surface having a plurality of grooves therein which intersect at various angles less than or equal to a predetermined maximum angle, said spatial filter comprising:

a first nontransmissive area having a predetermined width for blocking direct reflection of said source radiation beam from said planar surface; and at least one radially disposed substantially wedge-shaped transmissive area extending outward from said first nontransmissive area, said at least one radially disposed substantially wedge-shaped transmissive area having a width substantially equal to said predetermined width at a point proximate to said first nontransmissive area and increasing in width at a selected angle from a bisector of said radially disposed substantially wedge-shaped transmissive area, said selected angle being substantially equal to said predetermined maximum angle.

2. The spatial filter of claim 1, wherein said spatial filter includes two diametrically opposing radially disposed substantially wedge-shaped transmissive areas.

3. The spatial filter of claim 1, wherein said at least one radially disposed substantially wedge-shaped transmissive area is aligned with said scattered radiation.

4. A spatial filter for selectively filtering scattered radiation created as a result of a source radiation beam striking a planar surface having a plurality of grooves therein which intersect at various angles less than or equal to a predetermined maximum angle, said spatial filter comprising:

a first nontransmissive area having a predetermined width for blocking direct reflection of said source radiation beam from said planar surface; and at least one radially disposed substantially wedge-shaped nontransmissive area extending outward from said first nontransmissive area, said at least one radially disposed substantially wedge-shaped nontransmissive area having a width substantially equal to said predetermined width at a point proximate to said first nontransmissive area and increasing in width at a selected angle from a bisector of said radially disposed substantially wedge-shaped nontransmissive area, said selected angle being substantially equal to said predetermined maximum angle.

5. The spatial filter of claim 4, wherein said spatial filter includes two diametrically opposing radially disposed substantially wedge-shaped nontransmissive areas.

6. A system for monitoring surface structures on a planar surface having a plurality of surface structure types, including a plurality of grooves therein which intersect at various angles less than or equal to a predetermined maximum angle, said system comprising:

a radiation source for emitting a beam;

means for directing said beam to said planar surface along an optical axis perpendicular to said planar surface resulting in radiation scattered from said planar surface and a reference beam being specularly reflected from said planar surface;

means responsive to radiation scattered from said planar surface and producing a first signal representative thereof; and means for spatially filtering radiation scattered from said planar surface to allow only radiation from at least a selected one of said plurality of surface structure types to reach said means responsive to radiation scattered from said planar surface.

7. The system of claim 6 further comprising:

means responsive to said reference beam and producing a second signal thereof; and means for producing a final signal from said first signal and said second signal.

8. The system of claim 7, wherein said means for producing a final signal includes passing said first signal and said second signal through a division module.

9. The system of claim 6, wherein said means for spatially filtering radiation scattered from said planar surface includes a spatial filter configured to transmit light scattered by said plurality of grooves to said means responsive to said radiation scattered from said planar surface.

10. The system of claim 6, wherein said planar surface includes a defect and said means for spatially filtering radiation scattered from said planar surface includes a spatial filter configured to transmit radiation scattered by said defect to said means responsive to radiation scattered from said planar surface.

11. The system of claim 9, wherein said reference beam travels along an axis, said means responsive to radiation scattered from said planar surface is aligned off said axis allowing said reference beam to pass said means responsive to said radiation scattered from said planar surface; and said spatial filter comprises a nontransmissive area and at least one wedge-shaped transmissive area having a first end located proximately to said axis and a second end located distally to said axis, said at least one wedge-shaped transmissive area being radially disposed relative to said axis and having a predetermined width at said first end and increasing in width towards said outer edge at an angle from a bisector of said at least one wedge-shaped transmissive area, said angle having a vertex on said bisector and being equal to said predetermined maximum angle.

12. The system of claim 9, wherein said spatial filter is for selectively filtering scattered radiation, said spatial filter comprising:

a first nontransmissive area having a predetermined width;

at least one radially disposed substantially wedge-shaped transmissive area extending outward from said first nontransmissive area, said at least one radially disposed transmissive area having a width equal to said predetermined width at a point proximate to said first nontransmissive area and increasing in width at a selected angle from a bisector of said radially disposed transmissive area, said selected angle having a vertex on said bisector and being substantially equal to said predetermined maximum angle; and a second nontransmissive area surrounding said first transmissive area and said at least one radially disposed substantially wedge-shaped transmissive area.

13. The system of claim 10, wherein said spatial filter is a spatial filter for selectively filtering scattered radiation created as a result of a source radiation beam striking a planar surface having a plurality of grooves therein, which intersect at various angles and less than or equal to a predetermined maximum angle, said spatial filter comprising:

a first nontransmissive area having a predetermined width for blocking direct reflection of said source radiation beam from said planar surface;

at least one radially disposed substantially wedge-shaped nontransmissive area extending outward from said first nontransmissive area, said at least one radially disposed transmissive area having a width equal to said predetermined width at a point proximate to said first nontransmissive area and increasing in width at a selected angle from a bisector of said radially disposed transmissive area, said selected angle being substantially equal to said predetermined maximum angle; and a transmissive area surrounding said first nontransmissive area and said at least one radially disposed substantially wedge-shaped nontransmissive area.

14. The system of claim 6, wherein said radiation source is a coherent light source.

15. The system of claim 14, wherein said radiation source is a HeNe laser.

16. A spatial filter for transmitting scattered radiation created by a source radiation beam perpendicularly striking a planar surface having a plurality of grooves therein intersecting at various angles less than or equal to a predetermined maximum angle, to a detector and for blocking transmission of a reflected radiation beam traveling along an axis to said detector, said reflected beam originating from said source radiation beam reflected from said surface, said spatial filter comprising:

a nontransmissive area including a circular section having a circumferential edge and two points, a first point and a second point, diametrically opposed on said circumferential edge along a line vertically bisecting said circular section, said first point located above said second point, said circular section aligned coincidental with said axis of said reflected radiation beam, and said central section shaped to block transmission of said reflected radiation beam to said detector;

a first positioning line extending horizontally from said first point and a second positioning line extending horizontally from said second point;

a transmissive area having a wedge-shaped section extending away from said circular section, said wedge-shaped section having a first end proximally located to said circular section and terminating in a second end, said second larger than said first end, said section further defined by a first line extending from said first point away from said circular section to said second end at an angle from said first positioning line, wherein said angle is equal to said predetermined maximum angle and a second line extending from said second point away from said circular section to said second end at said angle from said second positioning line; and said nontransmissive area having a third section surrounding said circular section and said second section and configured to block radiation transmission of radiation not transmitted by said second to said detector.

* * * * *

UNITED STATES PATENT AND TRADEMARK OFFICE
CERTIFICATE OF CORRECTION

PATENT NO. : 5,155,372

DATED : Oct. 13, 1992

INVENTOR(S) : Arlen J. Bowen; David L. Erickson, Daniel W. Jewell, Venkat R. Koka It is certified that error appears in the above-identified patent and that said Letters Patent is hereby corrected as shown below:

Column 3, line 39, "Was" to --was--.

Column 3, line 40, "Would" to --would--.

Column 4, line 12, "Of" to --of--.

Column 4, line 29, "26" to --126--.

Column 4, line 30, "Of" to --of--.

Column 5, line 40, "Corresponding" should read --corresponding--.

Column 5, line 52, "19?" to --190--.

Column 6, line 9, "22" to --222--.

Signed and Sealed this

Fifth Day of October, 1993

BRUCE LEHMAN

Attest:

Attesting Officer

Commissioner of Patents and Trademarks